(12) United States Patent
Gilbeau (10) Patent No.: US 7,557,253 B2
(45) Date of Patent: Jul. 7, 2009

(54) METHOD FOR CONVERTING POLYHYDROXYLATED ALIPHATIC HYDROCARBONS INTO CHLOROHYDRINS

(75) Inventor: Patrick Gilbeau, Braine-le-Comte (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 11/915,056

(22) PCT Filed: May 19, 2006

(86) PCT No.: PCT/EP2006/062462

§ 371 (c)(1),
(2), (4) Date: Nov. 20, 2007

(87) PCT Pub. No.: WO2006/100320

PCT Pub. Date: Sep. 28, 2006

(65) Prior Publication Data

US 2008/0194848 A1  Aug. 14, 2008

Related U.S. Application Data

(60) Provisional application No. 60/734,635, filed on Nov. 8, 2005, provisional application No. 60/734,657, filed on Nov. 8, 2005, provisional application No. 60/734,636, filed on Nov. 8, 2005, provisional application No. 60/734,627, filed on Nov. 8, 2005, provisional application No. 60/734,634, filed on Nov. 8, 2005, provisional application No. 60/734,658, filed on Nov. 8, 2005, provisional application No. 60/734,637, filed on Nov. 8, 2005, provisional application No. 60/734,659, filed on Nov. 8, 2005.

(30) Foreign Application Priority Data

May 20, 2005  (EP) ................................. 05104321
May 20, 2005  (FR) ................................. 05 05120

(51) Int. Cl.
  *C07C 31/34* (2006.01)
  *C07D 301/27* (2006.01)
(52) U.S. Cl. ...................... 568/841; 549/518
(58) Field of Classification Search ............... 568/841; 549/518
See application file for complete search history.

(56) References Cited

U.S. PATENT DOCUMENTS

| 2,060,715 A | 11/1936 | Arvin |
| 2,063,891 A | 12/1936 | Dreyfus |
| 2,144,612 A | 1/1939 | Britton et al. |
| 2,198,600 A | 7/1940 | Britton et al. |
| 2,248,635 A | 7/1941 | Marple et al. |
| 2,319,876 A | 5/1943 | Moss |
| 2,444,333 A | 6/1948 | Castan |
| 2,829,124 A | 4/1958 | Napravnik et al. |
| 2,945,004 A | 7/1960 | Greenlee |
| 2,960,447 A | 11/1960 | Anderson et al. |
| 3,061,615 A | 10/1962 | Viriot et al. |
| 3,247,227 A | 4/1966 | White |
| 3,355,511 A | 11/1967 | Schwarzer |
| 3,385,908 A | 5/1968 | Schwarzer |
| 3,457,282 A | 7/1969 | Polak et al. |
| 3,865,886 A | 2/1975 | Schindler et al. |
| 3,867,166 A | 2/1975 | Sullivan |
| 3,968,178 A | 7/1976 | Obrecht et al. |
| 4,220,529 A | 9/1980 | Daude-Lagrave |
| 4,415,460 A | 11/1983 | Suciu et al. |
| 4,634,784 A | 1/1987 | Nagato et al. |
| 4,960,953 A | 10/1990 | Jakobson et al. |
| 4,973,763 A | 11/1990 | Jakobson et al. |
| 5,041,688 A | 8/1991 | Jakobson et al. |
| 5,344,945 A | 9/1994 | Grunchard |
| 5,359,094 A | 10/1994 | Teles et al. |
| 5,578,740 A | 11/1996 | Au et al. |
| 5,710,350 A | 1/1998 | Jeromin et al. |
| 5,731,476 A | 3/1998 | Shawl et al. |

(Continued)

FOREIGN PATENT DOCUMENTS

CA  1119320  8/2003

(Continued)

OTHER PUBLICATIONS

Armando Novelli, "The Preparation of Moni- and Dichlorohydrins of Glycerol," Anal. Farm. Bioqium, vol. 1, 1930, pp. 8-19 (with English Abstract).

(Continued)

*Primary Examiner*—Sikarl A Witherspoon
(74) *Attorney, Agent, or Firm*—Oblon, Spivak, McClelland, Maier & Neustadt, P.C.

(57) ABSTRACT

Process for preparing a chlorohydrin, wherein: (a) a polyhydroxylated aliphatic hydrocarbon, an ester of a polyhydroxylated aliphatic hydrocarbon or a mixture thereof is reacted with a chlorinating agent so as to give a mixture containing chlorohydrin, chlorohydrin esters and water, (b) at least a fraction of the mixture obtained in step (a) is subjected to a distillation and/or stripping treatment so as to give a part concentrated with water, with chlorohydrin and with chlorohydrin esters, (c) at least a fraction of the part obtained in step (b) is subjected to a separating operation in the presence of at least one additive so as to give a portion concentrated with chlorohydrin and with chlorohydrin esters and containing less than 40% by weight of water.

22 Claims, 1 Drawing Sheet

U.S. PATENT DOCUMENTS

| | | | |
|---|---|---|---|
| 5,908,946 | A | 6/1999 | Stern et al. |
| 6,142,458 | A | 11/2000 | Howk |
| 6,288,248 | B1 | 9/2001 | Strebelle et al. |
| 6,288,287 | B2 | 9/2001 | Ueoka et al. |
| 7,126,032 | B1 | 10/2006 | Aiken |
| 2001/0014763 | A1 | 8/2001 | Ueoka et al. |
| 2003/0209490 | A1 | 11/2003 | Camp et al. |
| 2004/0179987 | A1 | 9/2004 | Oku et al. |
| 2005/0261509 | A1 | 11/2005 | Delfort et al. |
| 2007/0112224 | A1 | 5/2007 | Krafft et al. |
| 2008/0194848 | A1 | 8/2008 | Gilbeau |

FOREIGN PATENT DOCUMENTS

| | | |
|---|---|---|
| CN | 1296003 A | 5/2001 |
| DE | 58396 | 8/1891 |
| DE | 180 668 | 1/1906 |
| DE | 197 308 | 11/1906 |
| DE | 238 341 | 3/1908 |
| DE | 1 041 488 | 10/1958 |
| DE | 1 075 103 | 2/1960 |
| DE | 1 226 554 | 10/1966 |
| DE | 37 21 003 | 6/1987 |
| DE | 102 03 914 | 1/2002 |
| DE | 197 309 | 4/2008 |
| EP | 0 347 618 | 12/1989 |
| EP | 0 421 379 | 4/1991 |
| EP | 0 518 765 | 12/1992 |
| EP | 0 568 389 | 11/1993 |
| EP | 0 582 201 | 2/1994 |
| EP | 0 919 551 | 6/1999 |
| EP | 1 059 278 | 12/2000 |
| EP | 1 106 237 | 6/2001 |
| EP | 1 153 887 | 11/2001 |
| EP | 0 561 441 | 9/2003 |
| EP | 1 752 435 | 2/2007 |
| EP | 1 752 436 | 2/2007 |
| EP | 1 760 060 | 3/2007 |
| EP | 1 762 556 | 3/2007 |
| EP | 1 770 081 | 4/2007 |
| EP | 1 772 446 | 4/2007 |
| EP | 1 775 278 | 4/2007 |
| FR | 1 476 073 | 4/1966 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 885 903 | 11/2006 |
| GB | 14 767 | 1/1914 |
| GB | 404 938 | 7/1932 |
| GB | 467 481 | 9/1935 |
| GB | 541357 | 11/1941 |
| GB | 679 536 | 9/1952 |
| GB | 736641 | 7/1953 |
| GB | 799 567 | 8/1958 |
| GB | 1083594 | 11/1964 |
| GB | 984446 | 2/1965 |
| GB | 984 633 | 3/1965 |
| GB | 1 387 668 | 3/1972 |
| GB | 1286893 | 8/1972 |
| GB | 1 414 976 | 11/1975 |
| GB | 2 173 496 | 10/1986 |
| GB | 702143 | 10/1990 |
| GB | 2 336 584 | 10/1999 |
| JP | 39-27230 | 11/1928 |
| JP | 56-29572 | 3/1981 |
| JP | 56-99432 | 8/1981 |
| JP | 62-242638 | 10/1987 |
| JP | 03-014527 | 1/1991 |
| JP | 3-223267 | 10/1991 |
| JP | 03-223267 | 10/1991 |
| JP | 04-089440 | 3/1992 |
| JP | 6-25196 | 4/1994 |
| JP | 6-184024 | 7/1994 |
| JP | 06-321852 | 11/1994 |
| JP | 8-59593 | 3/1996 |
| JP | 10-139700 | 5/1998 |
| JP | 2001-213827 | 8/2001 |
| JP | 2001-1261581 | 9/2001 |
| JP | 2002-02033 | 1/2002 |
| JP | 2002-363153 | 12/2002 |
| JP | 2003-81891 | 3/2003 |
| JP | 2003-89680 | 3/2003 |
| WO | WO 99/32397 | 7/1999 |
| WO | WO 01/86220 | 11/2001 |
| WO | WO 2005/021476 | 3/2005 |
| WO | WO 2005/054167 | 6/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100314 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 2006/106153 | 10/2006 |
| WO | WO 2006/106154 | 10/2006 |
| WO | WO 2006/106155 | 10/2006 |
| WO | WO 2007/005405 | 5/2007 |
| WO | WO 2007/054505 | 5/2007 |
| WO | WO 2007/144335 | 12/2007 |

OTHER PUBLICATIONS

Derwent Publications, AN 109:6092 CA, JP 62-242638 (Oct. 23, 1987).

Derwent Publications, AN 1987-338139 [48], JP 62-242638, (Oct. 23, 1987).

Kirk-Othmer Encyclopedia of Chemical Technology, Third Edition, vol. 4, Blood, Coagulants and Anticoagulants to Cardiovascular Agents.

J.B. Conant et al., "Glycerol a,y-Dichlorophydrin," Organic Syntheses Coll., vol. 1, p. 292, 1941.

I. Miyakawa et al., Nagoya Sangyo Kagaku Kenkyusho Kenkyu Hokoku, 10, 49-52 (1957).

Han Xiu-Ying et al., Shanxi Daxue Xueba Bianjibu, 2002, 25(4), 379-80).

Herman A. Bruson, et al., "Thermal Decomposition of Glyceryl Carbonates," Journal of the American Chemical Society, vol. 74, Apr. 1952 pp. 2100-2101.

Gibson., "The Preparation, Properties, and Uses of Glycerol Derivatives. Part III. The Chlorohydrins", Chemistry and Industry, Chemical Society, pp. 949-975, 1931.

Carre et al., "La Transformation Des Alcools Polyatomiques En Mono-Et En Polychlorhydrines au Moyen Du Chlorure De Thionyle", Bull. Soc. Chim. Fr., No. 49, pp. 1150-1154, 1931.

Fauconnier, "Preparation de L'Epichlorhydrine", Bull. Soc. Chim. Fr., No. 50, pp. 212-214, 1888.

"Industrially Important Epoxides", Ullmann's Encyclopedia of Industrial Chemistry, 5.ed., vol. A9, pp. 539-540.

Bonner et al., "The Composition of Constant Boiling Hydrochloric Acid at Pressures of 50 to 1220 Millimeters", Journal of American Chemical Society, vol. 52, pp. 633-635, 1930.

Muskopf et al., "Epoxy Resins", Ullmann's Encyclopedia of Industrial Chemistry, 5.ed, vol. A9, pp. 547-562.

Semendyava, N.D. et al., Khimicheskaya Promyshlennost, Seriya: Khornaya Promyshlennost (1981), 5, 21-2 (CA Summary) XP 002465275.

Rudnenko, E.V., et al., Kakokrasochnye Materialy I Ikh Primenenie (1988), 4, 69-71 (CA Summary) XP 002465276.
U.S. Appl. No. 11/914,879, filed Nov. 19, 2007, Gilbeau.
U.S. Appl. No. 11/915,059, filed Nov. 20, 2007, Gilbeau, et al.
U.S. Appl. No. 11/914,836, filed Nov. 19, 2007, Krafft, et al.
U.S. Appl. No. 11/915,067, filed Nov. 20, 2007, Krafft, et al.
U.S. Appl. No. 11/914,874, filed Nov. 19, 2007, Krafft, et al.
U.S. Appl. No. 11/914,862, filed Nov. 19, 2007, Gilbeau.
U.S. Appl. No. 11/914,856, filed Nov. 19, 2007, Krafft, et al.
U.S. Appl. No. 11/914,868, filed Nov. 19, 2007, Krafft.
U.S. Appl. No. 11/915,046, filed Nov. 20, 2007, Krafft, et al.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 60/560,676, filed Apr. 8, 2004, Unknown.
U.S. Appl. No. 60/734,659, filed Nov. 8, 2005, Unknown.
U.S. Appl. No. 60/734,627, filed Nov. 8, 2005, Unknown.
U.S. Appl. No. 60/734,657, filed Nov. 8, 2005, Unknown.
U.S. Appl. No. 60/734,658, filed Nov. 8, 2005, Unknown.
U.S. Appl. No. 60/734,635, filed Nov. 8, 2005, Unknown.
U.S. Appl. No. 60/734,634, filed Nov. 8, 2005, Unknown.
U.S. Appl. No. 60/734,637, filed Nov. 8, 2005, Unknown.
U.S. Appl. No. 60/734,636, filed Nov. 8, 2005, Unknown.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, field Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Unknown.
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870.
Oleoline, com, Glycerine Market report, Sep. 10, 2003, No. 62.
Notification Under Act. No. 100/2001, Coll. As Amended by Act No. 93/2004, Coll. To the extent of Annex No. 4, (Spolek) Nov. 30, 2004.
Documentation Under Act No. 100/2001 Coll. As amended by Act No. 93/2004 Coll in the scope of appendix No. 4 (Spolek) Jan. 11, 2005.
K. Weissermel and H J. Arpe in Industrial Organic Chemistry, Third, Completely Revised Edition, VCH, 1997, pp. 149,275.
Industrial Bioproducts: "Today and Tomorrow," Energetics, Inc. for the U.S. Department of Energy, Office of Energy Efficiency and Renewable Energy, Office of the Biomass Program, July 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429.
Ullmann's Encyclopedia of Industrial Chemistry, Fifth Completely REvised Edition, vol. A6, pp. 240-252.
Hancock, E.G., Propylene and its Industrial Derivatives, 1973, pp. 298-332.
K. Weissermel and H. J. Arpe in Industrial Organic Chemistry, Third, Completely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H. Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll,. as amended by later regulations of the project/intent combined process for the manufacture of epichlorohydrin (Spolek) Apr. 2005.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8, and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Perry's Chemical Engineers Handbook $7^{tth}$ Ed. $11^{th}$ Section, 1997.
Perry's Chemical Engineers Handbook $7^{tth}$ Ed. $13^{th}$ Section, 1997.
Perry's Chemical Engineers Handbook $7^{tth}$ Ed. $15^{th}$ Section, 1997.
Ullmann Encyclopedia Industr. Chem. $5^{th}$ Ed., vol. A23, 1993 pp. 635-636.
Ullmann Encyclopedia Industr. Chem. $5^{th}$ Ed., vol. A13, 1989 p. 289.
Ullmann Encyclopedia Industr. Chem. $5^{th}$ Ed., vol. A11, 1988 pp. 354-360.
U.S. Appl. No. 12/304,391, filed Dec. 12, 2008, Krafft, et al.
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and copies of similar passages but retrieved from the English $5^{th}$ Edition of the Book, 1987.

Figure 1

METHOD FOR CONVERTING POLYHYDROXYLATED ALIPHATIC HYDROCARBONS INTO CHLOROHYDRINS

The present patent application claims the benefit of patent application FR 05.05120 and of patent application EP 05104321.4, both filed on 20 May 2005, and of provisional U.S. patent applications 60/734,659, 60/734,627, 60/734,657, 60/734,658, 60/734,635, 60/734,634, 60/734,637 and 60/734,636, all filed on 8 Nov. 2005, the content of all of which is incorporated here by reference.

The present invention relates to a process for preparing a chlorohydrin.

Chlorohydrins are reaction intermediates in the preparation of epoxides. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

Application WO 2005/054167 of SOLVAY S. A. describes a process for preparing dichloropropanol by reacting glycerol with hydrogen chloride in the presence of a catalyst such as adipic acid. In this process a mixture of water and the dichloropropanol is separated off by azeotropic distillation, from which the dichloropropanol is subsequently separated by decantation. The dichloropropanol contains significant amounts of water, whose removal may give rise to an extra cost which is prohibitive for the economics of the process.

The aim of the invention is to provide a process for preparing a chlorohydrin that does not exhibit these drawbacks.

The invention accordingly provides a process for preparing a chlorohydrin, comprising the following steps:

(a) a polyhydroxylated aliphatic hydrocarbon, an ester of a polyhydroxylated aliphatic hydrocarbon or a mixture thereof is reacted with a chlorinating agent so as to give a mixture containing chlorohydrin, chlorohydrin esters and water (b) at least a fraction of the mixture obtained in step (a) is subjected to a distillation and/or stripping treatment so as to give a part concentrated with water, with chlorohydrin and with chlorohydrin esters (c) at least a fraction of the part obtained in step (b) is subjected to a separating operation in the presence of at least one additive so as to give a portion concentrated with chlorohydrin and with chlorohydrin esters and containing less than 40% by weight of water.

The separating operation of step (c) is preferably a decantation.

It has been found that, by using at least one additive in step (c) of the process according to the invention, it is possible to obtain more rapid demixing of the concentrated part obtained in step (b), to obtain more rapid decantation and to recover a portion concentrated with chlorohydrin and with chlorohydrin esters, and containing less water, than when a step (c) separating operation is carried out in the absence of the additive.

It has also been found, surprisingly, that the presence of the additive in the portion concentrated with chlorohydrin and with chlorohydrin esters that is obtained in step (c) does not disrupt the preparation processes downstream of the process for preparing the chlorohydrin, such as a process for preparing an epoxide by dehydrochlorinating the chlorohydrin, for example.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol(ethylene glycol), 1,2-propanediol(propylene glycol), 1,3-propanediol, 1-chloro-2,3-propanediol(chloropropanediol), 2-chloro-1,3-propanediol(chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of the polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon. Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The term "epoxide" is used herein to describe a compound containing at least one oxygen bridged on a carbon-carbon bond. Generally speaking, the carbon atoms of the carbon-carbon bond are adjacent and the compound may contain atoms other than carbon atoms and oxygen atoms, such as hydrogen atoms and halogens. The preferred epoxides are ethylene oxide, propylene oxide, glycidol, epichlorohydrin and mixtures of at least two thereof.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "natural glycerol" or "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used to prepare natural glycerol, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

In the process for preparing a chlorohydrin according to the invention, the polyhydroxylated aliphatic hydrocarbon may be as described in the patent application "Process for preparing chlorohydrin by converting polyhydroxylated aliphatic hydrocarbons", filed in the name of SOLVAY S A on the same day as the present application, and the content of which is incorporated here by reference.

Particular mention is made of a process for preparing a chlorohydrin wherein a polyhydroxylated aliphatic hydrocarbon, an ester of a polyhydroxylated aliphatic hydrocarbon or a mixture thereof whose total metal content, expressed in elemental form, is greater than or equal to 0.1 µg/kg and less than or equal to 1000 mg/kg is reacted with a chlorinating agent.

In the process according to the invention it is preferred to use glycerol obtained starting from renewable raw materials.

In the process according to the invention, the decantation operation results in at least two condensed phases being obtained, which are preferably liquid. The portion concentrated with chlorohydrin and with chlorohydrin esters and containing less than 40% by weight of water is preferably a liquid phase.

In the process according to the invention, the decantation operation leads with particular preference to two liquid phases being obtained. The phase which corresponds to the portion concentrated with chlorohydrin and with chlorohydrin esters will be referred to as the organic phase. The phase corresponding to the other portion will be referred to as the aqueous phase.

The weight ratio of the decanted phases varies depending on the nature of the chlorinating agent employed and on the amount of chlorinating agent in the part concentrated with water, with chlorohydrin and with chlorohydrin esters. The percentage of the mass of the organic phase in the total mass of organic phase and aqueous phase is generally greater than or equal to 1, often greater than or equal to 10, frequently greater than or equal to 20 and in particular greater than or equal to 40. This ratio is generally less than or equal to 99, often greater than or equal to 90, frequently less than or equal to 80 and in particular greater than or equal to 60.

The additive present in step (c) may be an acid, a salt or a mixture of the two. The acid and the salt may be organic or inorganic. Preference is given to using an inorganic salt or acid.

In a first embodiment of the process according to the invention an inorganic acid is used. The latter may be selected from hydrogen halides, sulphuric, sulphurous, sulphydric, nitric, nitrous, phosphoric, phosphorous, perchloric, chloric, chlorous, hypochlorous, carbonic, boric acid and mixtures thereof. Preference is given to using hydrogen halides and especially hydrogen chloride. When the acid is hydrogen chloride it may be used in gaseous form, in liquid form or in the form of aqueous or organic solutions. It is preferred to use it in gaseous form or in the form of aqueous solutions.

The amount of acid in the fraction of the concentrated part separated off in step (b) and subjected to the decantation operation is generally greater than or equal to 0.01 g/kg, often greater than or equal to 0.3 g/kg, frequently greater than or equal to 3 g/kg and in particular greater than or equal to 25 g/kg. This amount is generally less than or equal to 110 g/kg, frequently less than or equal to 80 g/kg and in particular less than or equal to 65 g/kg.

The amounts of acid in the aqueous and organic phases separated in step (c) may be readily deduced from the ternary compositional diagrams of the chlorhydrin/water/acid mixtures. A ternary diagram of this kind for the 1,3-dichloropropanol/water/hydrogen chloride mixture may be found in G. P. Gibson, The preparations, properties, and uses of glycerol derivatives. Part III. The chlorohydrins, pages 970 to 975.

The amount of acid in the aqueous phase separated in step (c) is generally greater than or equal to 30 g/kg, often greater than or equal to 50 g/kg, frequently greater than or equal to 75 g/kg and in particular greater than or equal to 100 g/kg. This amount is generally less than or equal to 170 g/kg, frequently less than or equal to 150 g/kg and in particular less than or equal to 130 g/kg.

In a first variant of the first embodiment of the process according to the invention, the acid is present in the part concentrated with water, with chlorohydrin and with chlorohydrin esters that is separated off in step (b).

In a second variant of the first embodiment of the process according to the invention, the acid is not present in the part concentrated with water, with chlorohydrin and with chlorohydrin esters that was separated off in step (b), and is added before this concentrated part is subjected to the decantation operation of step (c).

In a third variant of the first embodiment of the process according to the invention, the acid is present in the part concentrated with water, with chlorohydrin and with chlorohydrin esters that was separated off in step (b), and an additional amount thereof is added before this concentrated part is subjected to the decantation operation of step (c).

In a second embodiment of the process according to the invention, an inorganic salt is used, preferably a metal salt. The latter may be selected from metal halides, sulphates, hydrogen sulphates, sulphites, hydrogen sulphites, sulphides, hydrogen sulphides, nitrates, nitrites, phosphates, hydrogen phosphates, phosphites, hydrogen phosphites, perchlorates, chlorates, hypochlorites, carbonates, hydrogen carbonates, percarbonates, borates and perborates and mixtures thereof Preference is given to using alkali metal salts and/or alkaline earth metal salts. Alkali metal and/or alkaline earth metal halides, and especially sodium chloride, are preferred. The salts may be used in solid form or as aqueous or organic solutions. It is preferred to use them in the form of aqueous solutions.

In a first variant of the second embodiment, salts already formed are added to step (c) of the process according to the invention.

In a second variant of the second embodiment, the salts may also be generated in situ by reacting an acid, present in the fraction of the part obtained in step (b), with a basic compound. The basic compound may be an oxide, a hydroxide, a carbonate, a hydrogen carbonate or a mixture of least two thereof. Alkali metal and alkaline earth metal oxides, hydroxides, carbonates and hydrogen carbonates, and mixtures thereof, are preferred. Among the alkali metals and alkaline earth metals, preference is given to sodium, potassium and calcium. The advantages of this second variant are the coupling of the neutralization of the acid with the supply of salt required for the phase separation.

The amount of salt in the aqueous phase decanted in step (c) is generally greater than or equal to 0.4 g/kg, often greater than or equal to 5 g/kg, frequently greater than or equal to 30 g/kg and in particular greater than or equal to 65 g/kg. This amount is generally less than or equal to 450 g/kg, often less than or equal to 350 g/kg, frequently less than or equal to 200 g/kg and in particular less than or equal to 100 g/kg.

In this second embodiment of the process according to the invention, the salt is not present in the part concentrated with water, with chlorohydrin and with chlorohydrin esters that was separated off in step (b), and it is added before this part is subjected to the decantation operation of step (c).

In a third embodiment of the process according to the invention, a mixture is used of an inorganic salt and of an inorganic acid, as described earlier on above. Acids and salts having the same anion are preferred. Among these anions, the halides are particularly preferred, and the chloride is very particularly preferred.

In a first variant of this third embodiment of the process according to the invention, the salt and the acid are not present in the part concentrated with water, with chlorohydrin and with chlorohydrin esters that were separated off in step (b), and they are added before this concentrated part is subjected to the decantation operation of step (c).

In a second variant of this third embodiment of the process according to the invention, the salt is not present in the part concentrated with water, with chlorohydrin and with chlorohydrin esters that was separated off in step (b), and it is added before this concentrated part is subjected to the decantation operation of step (c), and the acid is present in the part concentrated with water and with chlorohydrin that was separated off in step (b).

In a third variant of this third embodiment of the process according to the invention, the salt is not present in the part concentrated with water, with chlorohydrin and with chlorohydrin esters that were separated off in step (b), and it is added before this concentrated part is subjected to the decantaion operation of step (c), and the acid is present in the part concentrated with water, with chlorohydrin and with chlorohydrin esters that were separated off in step (b) and an additional amount of the acid is added before this concentrated part is subjected to the decantation operation of step (c).

The ratio between the number of moles of chlorohydrin esters and the sum of the number of moles of chlorohydrin esters and of the number of moles of chlorohydrin is generally greater than or equal to 0.2, preferably less than or equal to 0.1 and more preferably less than or equal to 0.01.

In the process according to the invention, the decantation operation may be carried out under the effect of gravity or under the effect of a centrifugal force. It is preferred to carry out this operation under the effect of gravity.

In the process according to the invention, the decantation operation is carried out at a temperature which is generally less than or equal to 100° C., often less than or equal to 80° C., frequently less than or equal to 70° C. and in particular less than or equal to 50° C. This temperature is generally greater than or equal to 4° C. and often greater than or equal to 10° C.

In the process according to the invention, the decantation time is generally less than or equal to 120 min, preferably less than or equal to 90 min and with particular preference less than or equal to 60 min. This time is defined as the volume of the phase separator relative to the volume flow rate of liquid supplied to the phase separator.

The amount of water in the portion concentrated with chlorohydrin and with chlorohydrin esters may be readily deduced from the ternary compositional diagrams of the chlorohydrin/water/acid mixtures. A ternary diagram of this kind for the 1,3-dichloropropanol/water/hydrogen chloride mixture may be found in G. P. Gibson, The preparations, properties, and uses of glycerol derivatives. Part III. The chlorohydrins, pages 970 to 975.

The amount of water in the fraction of the portion concentrated with chlorohydrin and with esters of chlorohydrin that is obtained in step (c) is preferably less than or equal to 20% by weight and often less than or equal to 10% by weight, frequently less than or equal to 5% by weight, in particular less than or equal to 1.5% by weight and very specifically less than or equal to 1% by weight.

In the process for preparing a chlorohydrin according to the invention, the polyhydroxylated aliphatic hydrocarbon, the ester of polyhydroxylated aliphatic hydrocarbon or the mixture thereof may be a crude product or a purified product, such as are specifically disclosed in application WO 2005/054167 of SOLVAY S. A., from page 2 line 8 to page 4 line 2.

In the process for preparing a chlorohydrin according to the invention, the polyhydroxylated aliphatic hydrocarbon may be a polyhydroxylated aliphatic hydrocarbon, an ester of a polyhydroxylated aliphatic hydrocarbon or a mixture thereof whose alkali metal and/or alkaline earth metal content may be less than or equal to 5 g/kg, as described in the application entitled "Process for preparing a chlorohydrin by chlorinating a polyhydroxylated aliphatic hydrocarbon", filed in the name of SOLVAY S. A. on the same day as the present application, and whose content is incorporated here by reference. The alkali metals may be selected from lithium, sodium, potassium, rubidium and cesium and the alkaline earth metals may be selected from magnesium, calcium, strontium and barium.

In the process according to the invention, the alkali metal and/or alkaline earth metal content of the polyhydroxylated aliphatic hydrocarbon, the ester of polyhydroxylated aliphatic hydrocarbon or the mixture thereof is less than or equal to 5 g/kg, often less than or equal to 1 g/kg, more particularly less than or equal to 0.5 g/kg and in certain cases less than or equal to 0.01 g/kg. The alkali metal and/or alkaline earth metal content of the glycerol is generally greater than or equal to 0.1 µg/kg.

In the process according to the invention the alkali metals are generally lithium, sodium, potassium and cesium, often sodium and potassium, and frequently sodium.

In the process for preparing a chlorohydrin according to the invention, the lithium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the sodium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the potassium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the rubidium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the cesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkaline earth metal elements are generally magnesium, calcium, strontium and barium, often magnesium and calcium and frequently calcium.

In the process according to the invention, the magnesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the calcium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the strontium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the barium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkali and/or alkaline earth metals are generally present in the form of salts, frequently in the form of chlorides, sulphates and mixtures thereof. Sodium chloride is the most often encountered.

In the process for preparing a chlorohydrin according to the invention, the chlorinating agent may be as described in application WO 2005/054167 of SOLVAY SA, from page 4 line 25 to page 6 line 2.

In the process for preparing a chlorohydrin according to the invention, the chlorinating agent may be hydrogen chloride as described in application WO 2005/054167 of SOLVAY S. A., from page 4 line 30 to page 6 line 2.

Particular mention is made of a chlorinating agent which may be aqueous hydrochloric acid or hydrogen chloride which is preferably anhydrous. The hydrogen chloride may come from a process for pyrolysing organic chlorine compounds, such as, for example, from a vinyl chloride preparation, from a process for preparing 4,4-methylenediphenyl diisocyanate (MDI) or toluene diisocyanate (TDI), from metal pickling processes or from the reaction of an inorganic acid such as sulphuric or phosphoric acid with a metal chloride such as sodium chloride, potassium chloride or calcium chloride.

In one advantageous embodiment of the process for preparing a chlorohydrin according to the invention, the chlorinating agent is gaseous hydrogen chloride or an aqueous solution of hydrogen chloride, or a combination of the two.

In the process for preparing a chlorohydrin according to the invention, the hydrogen chloride may be an aqueous solution of hydrogen chloride or the hydrogen chloride, preferably anhydrous, obtained from a plant for preparing allyl chloride and/or for preparing chloromethanes and/or for chlorinolysis and/or for high-temperature oxidation of chlorine compounds, as described in the application entitled "Process for preparing a chlorohydrin by reacting a polyhydroxylated aliphatic hydrocarbon with a chlorinating agent", filed in the name of SOLVAY S. A. on the same day as the present application, and the content of which is incorporated here by reference.

Particular mention is made of a process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

Particular mention is made of an organic hydrocarbon compound selected from saturated and unsaturated aliphatic and aromatic hydrocarbons and mixtures thereof.

Particular mention is made of an unsaturated aliphatic hydrocarbon selected from acetylene, ethylene, propylene, butene, propadiene, methylacetylene and mixtures thereof, of a saturated aliphatic hydrocarbon selected from methane, ethane, propane, butane and mixtures thereof and of an aromatic hydrocarbon which is benzene.

Particular mention is made of an organic halogen compound which is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

Particular mention is made of an organic halogen compound which is an organic fluorine compound selected from fluoromethanes, fluoroethanes, vinyl fluoride, vinylidene fluoride and mixtures thereof.

Particular mention is made of an organic oxygen compound selected from alcohols, chloroalcohols, chloroethers and mixtures thereof.

Particular mention is made of a metal selected from alkali metals, alkaline earth metals, iron, nickel, copper, lead, arsenic, cobalt, titanium, cadmium, antimony, mercury, zinc, selenium, aluminium, bismuth and mixtures thereof. Mention is made more particularly of a process wherein the chlorinating agent is obtained at least partly from a process for preparing allyl chloride and/or a process for preparing chloromethanes and/or a process of chlorinolysis and/or a process for oxidizing chlorine compounds at a temperature greater than or equal to 800° C.

In one particularly advantageous embodiment of the process for preparing a chlorohydrin according to the invention, the hydrogen chloride is an aqueous solution of hydrogen chloride and does not contain gaseous hydrogen chloride.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reactor as described in application WO 2005/054167 of SOLVAY S. A. on page 6 lines 3 to 23.

Mention is made particularly of a plant made from or covered with materials which are resistant, under the conditions of the reaction, to the chlorinating agents, in particular to the hydrogen chloride. Mention is made more particularly of a plant made of enamelled steel or of tantalum.

In the process for preparing a chlorohydrin according to the invention, the reaction of the polyhydroxylated aliphatic hydrocarbon, the ester of the polyhydroxylated aliphatic hydrocarbon or the mixture thereof with the chlorinating agent may be carried out in apparatus which is made of or covered with materials that are resistant to chlorinating agents, as described in the patent application entitled "Process for preparing a chlorohydrin in corrosion-resistant apparatus", filed in the name of SOLVAY S. A. on the same day as the present application, and the content of which is incorporated here by reference.

Particular mention is made of a process for preparing a chlorohydrin that includes a step in which a polyhydroxylated aliphatic hydrocarbon, an ester of a polyhydroxylated aliphatic hydrocarbon or a mixture thereof is subjected to reaction with a chlorinating agent containing hydrogen chloride and to at least one other step carried out in an apparatus made of or covered with materials resistant to the chlorinating agent, under the conditions in which that step is realized. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and unimpregnated and impregnated graphite.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reaction medium as described in the application entitled "Continuous process for preparing chlorohydrins", filed in the name of SOLVAY S A on the same day as the present application, and the content of which is incorporated here by reference.

Particular mention is made of a continuous process for producing chlorohydrin in which a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition comprises polyhydroxylated aliphatic hydrocarbon and esters of polyhydroxylated aliphatic hydrocarbon for which the sum of the amounts, expressed in moles of polyhydroxylated aliphatic hydrocarbon, is greater than 1.1 mol % and less than or equal to 30 mol %, the percentage being based on the organic part of the liquid reaction medium.

The organic part of the liquid reaction medium consists of all of the organic compounds of the liquid reaction medium, in other words the compounds whose molecule contains at least one carbon atom.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out in the presence of a catalyst as described in application WO 2005/054167 of SOLVAY S. A. from page 6 line 28 to page 8 line 5.

Mention is made particularly of a catalyst based on a carboxylic acid or on a carboxylic acid derivative having an atmospheric boiling point of greater than or equal to 200° C., especially adipic acid and derivatives of adipic acid.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out at a catalyst concentration, temperature and pressure and for residence times as described in the application WO 2005/054167 of SOLVAY S. A. from page 8 line 6 to page 10 line 10.

Mention is made particularly of a temperature of at least 20° C. and not more than 160° C., of a pressure of at least 0.3 bar and not more than 100 bar and of a residence time of at least 1 h and not more than 50 h.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a solvent as described in application WO 2005/054167 of SOLVAY S. A. at page 11 lines 12 to 36.

Mention is made particularly of organic solvents such as a chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol and mixtures of chloropropanediol and dichloropropanol, or heavy products of the reaction such as at least partially chlorinated and/or esterified oligomers of the polyhydroxylated aliphatic hydrocarbon.

In the process for preparing a chlorohydrin according to the invention, the reaction of the polyhydroxylated aliphatic hydrocarbon, the ester of polyhydroxylated aliphatic hydrocarbon or a mixture thereof with the chlorinating agent may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY S. A. on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon and having a boiling temperature under a pressure of 1 bar absolute of at least 15° C. more than the boiling temperature of the chlorohydrin under a pressure of 1 bar absolute.

In the process for preparing a chlorohydrin according to the invention the reaction of the polyhydroxylated aliphatic hydrocarbon, the ester of polyhydroxylated aliphatic hydrocarbon or the mixture thereof with the chlorinating agent is preferably carried out in a liquid reaction medium. The liquid reaction medium may be a single-phase or multi-phase medium.

The liquid reaction medium is composed of all of the dissolved or dispersed solid compounds, dissolved or dispersed liquid compounds and dissolved or dispersed gaseous compounds at the temperature of the reaction.

The reaction medium comprises the reactants, the catalyst, the solvent, the impurities present in the reactants, in the solvent and in the catalyst, the reaction intermediates, the products and the by-products of the reaction.

By reactants are meant the polyhydroxylated aliphatic hydrocarbon, the ester of polyhydroxylated aliphatic hydrocarbon and the chlorinating agent.

Among the impurities present in the polyhydroxylated aliphatic hydrocarbon mention may be made of carboxylic acids, salts of carboxylic acids, esters of fatty acid with the polyhydroxylated aliphatic hydrocarbon, esters of fatty acids with the alcohols used in the transesterification, and inorganic salts such as alkali metal or alkaline earth metal sulphates and chlorides.

When the polyhydroxylated aliphatic hydrocarbon is glycerol, the impurities in the glycerol that may be mentioned include carboxylic acids, salts of carboxylic acids, fatty acid esters such as mono-, di- and triglycerides, esters of fatty acids with the alcohols used in the transesterification and inorganic salts such as alkali metal or alkaline earth metal sulphates and chlorides.

Among the reaction intermediates mention may be made of monochlorohydrins of the polyhydroxylated aliphatic hydrocarbon and their esters and/or polyesters, the esters and/or polyesters of the polyhydroxylated aliphatic hydrocarbon and the esters of polychlorohydrins.

When the chlorohydrin is dichloropropanol, the reaction intermediates that may be mentioned include glycerol monochlorohydrin and its esters and/or polyesters, the esters and/or polyesters of glycerol and the esters of dichloropropanol.

The ester of polyhydroxylated aliphatic hydrocarbon may therefore be, at each instance, a reactant, an impurity of the polyhydroxylated aliphatic hydrocarbon or a reaction intermediate.

By products of the reaction are meant the chlorohydrin and water. The water may be the water formed in the chlorination reaction and/or water introduced into the process, for example via the polyhydroxylated aliphatic hydrocarbon and/or the chlorinating agent, as described in the application WO 2005/054167 of SOLVAY S. A. at page 2 lines 22 to 28 to page 3 lines 20 to 25, at page 5 lines 7 to 31 and at page 12 lines 14 to 19.

Among the by-products mention may be made for example of the partially chlorinated and/or esterified oligomers of the polyhydroxylated aliphatic hydrocarbon.

When the polyhydroxylated aliphatic hydrocarbon is glycerol, the by-products that may be mentioned include, for example, the partially chlorinated and/or esterified oligomers of glycerol.

The reaction intermediates and the by-products may be formed in the different steps of the process, such as, for example, during the step of preparing the chlorohydrin and during the steps of separating off the chlorohydrin.

The liquid reaction mixture may therefore contain the polyhydroxylated aliphatic hydrocarbon, the chlorinating agent in solution or dispersion in the form of bubbles, the catalyst, the solvent, the impurities present in the reactants, in the solvent and in the catalyst, such as dissolved or solid salts, for example, the reaction intermediates, the products and the by-products of the reaction.

Steps (a), (b) and (c) of the process for preparing a chlorohydrin according to the invention may be conducted independently in batch mode or in continuous mode. The continuous mode for the three steps is particularly preferred.

In the process for preparing a chlorohydrin according to the invention, the reaction of chlorinating the polyhydroxylated aliphatic hydrocarbon, the ester of polyhydroxylated aliphatic hydrocarbon or the mixture thereof may be carried out in the presence of an organic acid. The organic acid may be a product originating from the process for preparing the polyhydroxylated aliphatic hydrocarbon or a product not originating from this process. In this latter case the product in question may be an organic acid which is used in order to catalyse the reaction of the polyhydroxylated aliphatic hydrocarbon with the chlorinating agent. The organic acid may also be a mixture of an organic acid originating from the process for preparing the polyhydroxylated aliphatic hydrocarbon, and of an organic acid not originating from the process for preparing the polyhydroxylated aliphatic hydrocarbon.

In the process according to the invention the esters of the polyhydroxylated aliphatic hydrocarbon may originate from the reaction between the polyhydroxylated aliphatic hydrocarbon and the organic acid, before, during or within the steps which follow the reaction with the chlorinating agent. The organic acid is as defined above.

In the process according to the invention, the separation of the chlorohydrin and of the other compounds from the reaction mixture may be carried out in accordance with the methods as described in the application WO 2005/054167 of SOLVAY S. A. from page 12 line 1 to page 16 line 35 and page 18 lines 6 to 13. These other compounds are those mentioned above and include unconsumed reactants, the impurities present in the reactants, the catalyst, the solvent, the reaction intermediates, the water and the by-products of the reaction.

Particular mention is made of separation by azeotropic distillation of a water/chlorohydrin/chlorinating agent mixture under conditions which minimize the losses of chlorinating agent, followed by isolation of the chlorohydrin by decantation.

In the process for preparing a chlorohydrin according to the invention, the isolation of the chlorohydrin and of the other compounds from the reaction mixture may be carried out in accordance with methods of the kind described in patent application EP 05104321.4, filed in the name of SOLVAY S. A. on 20 May 2005 and the content of which is incorporated here by reference. Particular mention is made of a separation method including at least one separating operation intended to remove the salt from the liquid phase.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of the polyhydroxylated aliphatic hydrocarbon or a mixture thereof that is used comprises at least one solid or dissolved metal salt, the process including a separation operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of a polyhydroxylated aliphatic hydrocarbon or a mixture thereof that is used comprises at least one chloride and/or a sodium and/or potassium sulphate and in which the separating operation intended to remove part of the metal salt is a filtering operation. Particular mention is also made of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) continuously or periodically, a fraction of the reaction mixture containing at least water and the chlorohydrin is removed, (c) at least a part of the fraction obtained in step (b) is introduced into a distillation step and (d) the reflux ratio of the distillation step is controlled by providing water to the said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) continuously or periodically, a fraction of the reaction mixture containing at least water and chlorohydrin is removed, (c) at least part of the fraction obtained in step (b) is introduced into a distillation step in which the ratio between the hydrogen chloride concentration and the water concentration in the fraction introduced into the distillation step is smaller than the hydrogen chloride/water concentration ratio in the binary azeotropic hydrogen chloride/water composition at the distillation temperature and pressure.

In the process for preparing a chlorohydrin according to the invention, the separation of the chlorohydrin and of the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin" filed in the name of SOLVAY S. A. on the same day as the present application and the content of which is incorporated here by reference.

Particular mention is made of a process for preparing a chlorohydrin which comprises the following steps: (a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin, (b) at least part of the mixture obtained in (a) is subjected to one or more treatments subsequent to step (a), and (c) the polyhydroxylated aliphatic hydrocarbon is added to at least one of the steps subsequent to step (a), in order to react at a temperature greater than or equal to 20° C. with the esters of the chlorohydrin, so as to form, at least partly, esters of the polyhydroxylated aliphatic hydrocarbon. Mention is made more particularly of a process in which the polyhydroxylated aliphatic hydrocarbon is glycerol and the chlorohydrin is dichloropropanol.

In the process for preparing a chlorohydrin according to the invention, the separation of the chlorohydrin and the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin starting from a polyhydroxylated aliphatic hydrocarbon", filed in the name of SOLVAY S. A. on the same day as the present application, and the content of which is incorporated here by reference.

Particular mention is made of a process for preparing chlorohydrin by reacting a polyhydroxylated aliphatic hydrocarbon, an ester of a polyhydroxylated aliphatic hydrocarbon or a mixture thereof with a chlorinating agent in a reactor which is supplied with one or more liquid streams containing less than 50% by weight of the polyhydroxylated aliphatic hydrocarbon, of the ester of polyhydroxylated aliphatic hydrocarbon or of the mixture thereof relative to the weight of the entirety of the liquid streams introduced into the reactor. More particular mention is made of a process comprising the following steps: (a) a polyhydroxylated aliphatic hydrocarbon, an ester of a polyhydroxylated aliphatic hydrocarbon or a mixture thereof is reacted with a chlorinating agent so as to give at least one mixture containing the chlorohydrin, water and the chlorinating agent, (b) at least a fraction of the mixture formed in step (a) is removed, and (c) the fraction removed in step (b) is subjected to an operation of distillation and/or stripping wherein the polyhydroxylated aliphatic hydrocarbon is added in order to isolate, from the fraction removed in step (b), a mixture containing water and the chlorohydrin and exhibiting a reduced chlorinating agent content as compared with the fraction removed in step (b).

In the process for preparing a chlorohydrin according to the invention, the isolation and the treatment of the other compounds of the reaction mixture may be carried out in accordance with methods as described in the application entitled "Process for preparing a chlorohydrin by chlorinating a polyhydroxylated aliphatic hydrocarbon", filed in the name of SOLVAY S. A. on the same day as the present application. A preferred treatment consists in subjecting a fraction of the by-products of the reaction to a high-temperature oxidation.

Particular mention is made of a process for preparing a chlorohydrin that comprises the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, a chlorinating agent and an organic acid are reacted so as to give a mixture containing at least the chlorohydrin and by-products, (b) at least a portion of the mixture obtained in step (a) is subjected to one or more treatments in steps subsequent to step (a), and (c) at least one of the steps subsequent to step (a) consists in an oxidation at a temperature greater than or equal to 800° C. More particular mention is made of a process wherein, in the subsequent step, a portion of the mixture obtained in step (a) is removed and this portion is subjected to oxidation at a temperature greater than or equal to 800° C. in the course of the removal. Particular mention is also made of a process wherein the treatment of step (b) is a separating operation selected from phase separation, filtration, centrifugation, extraction, washing, evaporation, stripping, distillation, and adsorption operations or the combinations of at least two of these operations.

In the process according to the invention, when the chlorohydrin is chloropropanol, it is generally employed in the form of a mixture of compounds comprising the isomers of 1-chloropropan-2-ol and 2-chloropropan-1-ol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanol, such as residual reactants, reaction by-products, solvents and, in particular, water.

The mass ratio of the isomers, 1-chloropropan-2-ol and 2-chloropropan-1-ol, is commonly greater than or equal to 0.01, preferably greater than or equal to 0.4. This ratio is commonly less than or equal to 99 and preferably less than or equal to 25.

In the process according to the invention, when the chlorohydrin is chloroethanol, it is generally employed in the form of a mixture of compounds comprising the 2-chloroethanol isomer. This mixture generally contains more than 1% by weight of the isomer, preferably more than 5% by weight and particularly more than 50%. The mixture commonly contains less than 99.9% by weight of the isomer, preferably less than 95% by weight and more particularly less than 90% by weight. The other constituents of the mixture may be compounds originating from the processes for preparing the chloroethanol, such as residual reactants, reaction by-products, solvents and, in particular, water.

In the process according to the invention, when the chlorohydrin is chloropropanediol, it is generally employed in the form of a mixture of compounds comprising the isomers of 1-chloropropane-2,3-diol and 2-chloropropane-1,3-diol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanediol, such as residual reactions, reaction by-products, solvents and, in particular, water.

The mass ratio between the 1-chloropropane-2,3-diol and 2-chloropropane-1,3-diol isomers is commonly greater than or equal to 0.01, preferably greater than or equal to 0.4. This ratio is commonly less than or equal to 99 and preferably less than or equal to 25.

In the process according to the invention, when the chlorohydrin is dichloropropanol, it is generally employed in the form of a mixture of compounds comprising the isomers of 1,3-dichloropropan-2-ol and 2,3-dichloropropan-1-ol. This mixture generally contains more than 1% by weight of the two isomers, preferably more than 5% by weight and in particular more than 50%. The mixture commonly contains less than 99.9% by weight of the two isomers, preferably less than 95% by weight and more particularly less than 90% by weight. The other constituents of the mixture may be compounds originating from the processes for preparing the dichloropropanol, such as residual reactants, reaction by-products, solvents and, in particular, water.

The mass ratio between the 1,3-dichloropropan-2-ol and 2,3-dichloropropan-1-ol isomers is commonly greater than or equal to 0.01, often greater than or equal to 0.4, frequently greater than or equal to 1.5, preferably greater than or equal to 3.0, more preferredly greater than or equal to 7.0 and with very particular preference greater than or equal to 20.0. This ratio is commonly less than or equal to 99 and preferably less than or equal to 25.

The chlorohydrin obtained in the process according to the invention may include a heightened amount of halogenated ketones, in particular of chloroacetone, as described in the patent application FR 05.05120 of 20 May 2005, filed in the name of the applicant, and the content of which is incorporated here by reference. The halogenated ketone content may be reduced by subjecting the chlorohydrin obtained in the process according to the invention to an azeotropic distillation in the presence of water or by subjecting the chlorohydrin to a dehydrochlorination treatment as described in this application from page 4 line 1 to page 6 line 35.

Particular mention is made of a process for preparing an epoxide wherein halogenated ketones are formed as by-products and which comprises at least one treatment of removal of at least a portion of the halogenated ketones formed. Mention is made more particularly of a process for preparing an epoxide by dehydrochlorinating a chlorohydrin of which at least one fraction is prepared by chlorinating a polyhydroxylated aliphatic hydrocarbon, an ester of a polyhydroxylated aliphatic hydrocarbon or a mixture thereof, a treatment of dehydrochlorination and a treatment by azeotropic distillation of a water/halogenated ketone mixture, which are intended to remove at least a portion of the halogenated ketones formed, and a process for preparing epichlorohydrin wherein the halogenated ketone formed is chloroacetone.

The chlorohydrin obtained in the process according to the invention may be subjected to a dehydrochlorination reaction in order to produce an epoxide, as described in the patent applications WO 2005/054167 and FR 05.05120, both filed in the name of SOLVAY S. A.

The dehydrochlorination of the chlorohydrin may be carried out as described in the application entitled "Process for preparing an epoxide starting from a polyhydroxylated aliphatic hydrocarbon and a chlorinating agent", filed in the name of SOLVAY S. A. on the same day as the present application, and the content of which is incorporated here by reference.

Particular mention is made of a process for preparing an epoxide wherein a reaction mixture resulting from the reaction between a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without intermediate treatment.

Mention is also made of the preparation of an epoxide that comprises the following steps:
(a) a polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture,
(b) at least a fraction of the reaction mixture obtained in step (a), this fraction having the same composition as the reaction mixture obtained in step (a), is subjected to one or more treatments in steps subsequent to step (a),
(c) a basic compound is added to at least one of the steps subsequent to step (a) in order to react at least partly with the chlorohydrin, the chlorohydrin esters, the chlorinating agent and the organic acid so as to form the epoxide and salts.

The process for preparing the chlorohydrin according to the invention may be integrated within an overall plan for preparation of an epoxide, as described in the application entitled "Process for preparing an epoxide starting from a chlorohydrin", filed in the name of SOLVAY S. A. on the same day as the present application, and the content of which is incorporated here by reference.

Particular mention is made of a process for preparing an epoxide that comprises at least one step of purification of the epoxide formed, the epoxide being at least partly prepared by a process of dehydrochlorinating a chlorohydrin, the latter being at least partly prepared by a process of chlorinating a polyhydroxylated aliphatic hydrocarbon, an ester of a polyhydroxylated aliphatic hydrocarbon or a mixture thereof.

When the epoxide is epichlorohydrin, the preparation of the epoxide may be integrated into a process for preparing epoxy resins.

In the process according to the invention, the polyhydroxylated aliphatic hydrocarbon is preferably glycerol and the chlorohydrin is preferably dichloropropanol.

When the chlorohydrin is dichloropropanol, the process according to the invention may be followed by the preparation of epichlorohydrin by dehydrochlorination of dichloropropanol, and the epichlorohydrin may be used in the preparation of epoxy resins.

Steps (b) and (c) of the process according to the invention also apply to a mixture containing the chlorohydrin, chlorohydrin esters and water that is obtained by reactions other than the reaction of a polyhydroxylated aliphatic hydrocarbon with a chlorinating agent; for example, by hypochlorination of an olefin such as ethylene, propylene or allyl chloride or by chlorination of an alcohol, such as allyl alcohol, for example.

Figure 1:
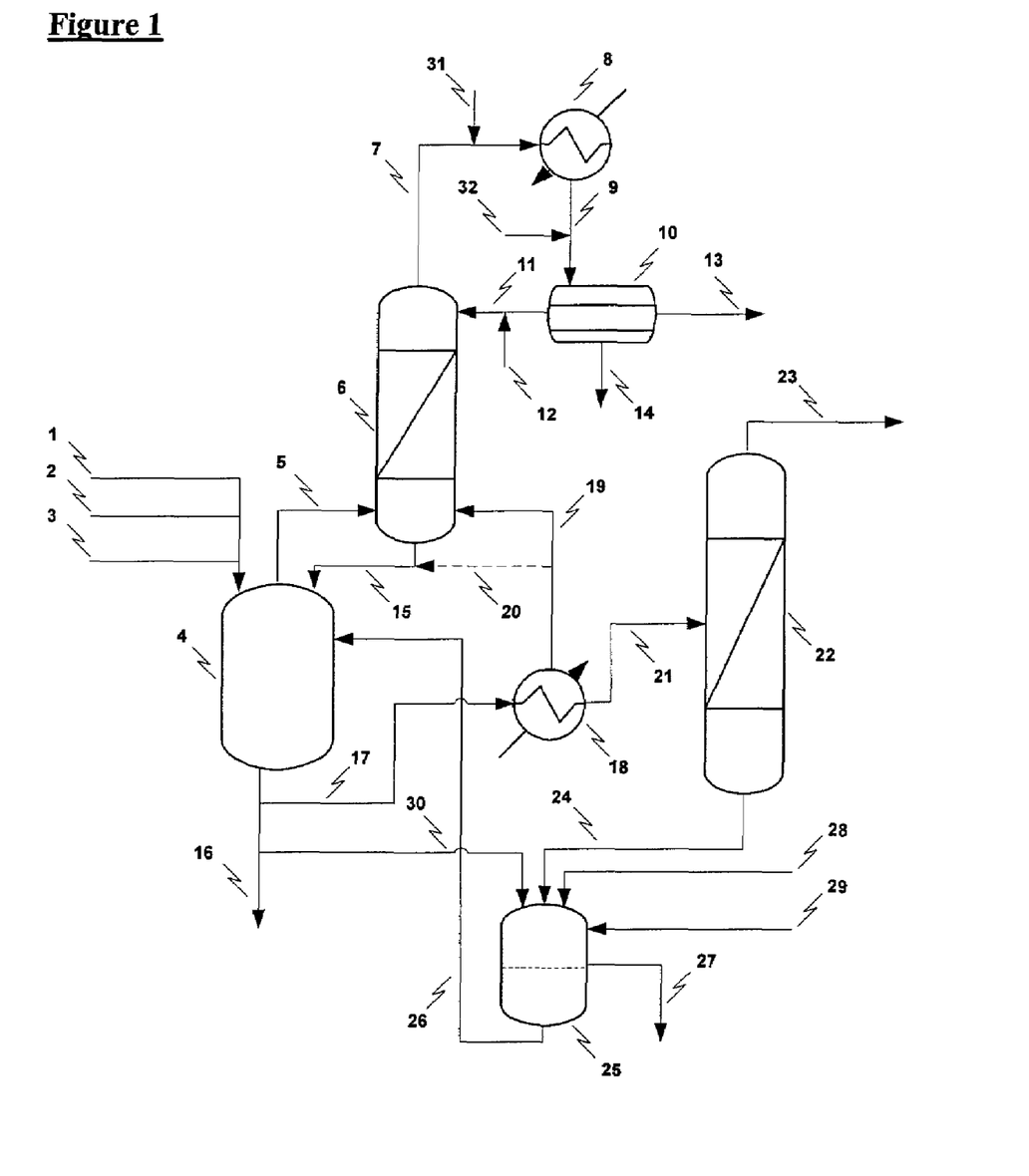
FIG. 1 shows a particular scheme of plant which can be used to implement the preparation process according to the invention.

A reactor (4) is supplied in continuous mode or in batch mode with a polyhydroxylated aliphatic hydrocarbon, an ester of a polyhydroxylated aliphatic hydrocarbon or a mixture thereof via line (1) and with catalyst via line (2); the chlorinating agent is supplied in continuous mode or in batch mode via line (3); a distillation column (6) is supplied via line (5) with vapors produced in reactor (4); a stream is taken off from column (6) via line (7) and is introduced into a condenser (8); the stream obtained from the condenser is introduced via line (9) into a phase separator (10), in which aqueous and organic phases are separated. An additive may be introduced into the stream from line (7) via line (31) and/or into the stream from line (9) via line (32). A fraction of the separated aqueous phase is optionally recycled via line (11) to the top of the column in order to maintain the reflux. Water is introduced into line (11) via line (12). The production of chlorohydrin is distributed between the organic phase taken off via line (14) and the aqueous phase taken off via line (13). The residue from column (6) may be recycled to reactor (4) via line (15). A fraction of the heavy products is taken off from reactor (4) via the purge (16) and is introduced via line (17) into an evaporator (18), in which a partial evaporation operation is carried out, for example by heating or by gas scavenging with nitrogen or with water vapor; the gas phase containing the majority of the chlorinating agent of stream (17) is recycled via line (19) to column (6) or via line (20) to reactor (4); a distillation or stripping column (22) is supplied with the liquid phase coming from the stripping apparatus (18) via line (21); and the major part of the chlorohydrin is recovered at the top of column (22) via line (23).

Optionally, the heavy by-products obtained from column (22) are passed via line (24) into the filtering column (25), in which liquid and solid phases are separated, and a fraction of the liquid phase is recycled via line (26) to reactor (4). The solid may be taken off from the filtering unit (25) via line (27) in the form of a solid or a solution. Solvents may be added to filtering unit (25) via lines (28) and (29) for the washing and/or dissolving of the solid, and may be taken off via line (27). Optionally, a stream is taken off from purge (16) and introduced via line (30) into filtering column (25). The stripping apparatus (18) and distillation column (22) are in that case short-circuited.

The examples below are intended to illustrate the invention without, however, imposing any limitation thereon.

EXAMPLES 1 TO 18

In Accordance with the Invention

In a separating funnel whose base consists of a graduated cylindrical tube, water, 1,3-dichloropropanol and aqueous solutions of hydrogen chloride (Examples 1 to 5), perchloric acid (Examples 6 to 10), sodium chloride (Examples 11 to 16) and calcium chloride (Examples 17 and 18), the concentrations of which are given respectively in Tables 1 to 4, are mixed vigorously for 15 minutes at 25° C. Stirring was halted and then the mixture was allowed to separate into phases. A measurement was made of the height of the interface between the phases over time. Time zero corresponds to the halt in stirring. The time after which the height of the interface is constant to +/−1 mm constitutes the duration of the phase separating operation.

In the organic phase, the amounts of hydrogen chloride and of perchloric acid are measured by acid-based titration, the amount of sodium chloride and of calcium chloride by argentimetric titration or by atomic emission spectrometry coupled with plasma induction (ICP-AES), depending, respectively, on whether the salt concentration is high or low, and the water content by the Karl-Fischer method. The dichloropropanol content is calculated by difference. In the aqueous phase, the amounts of hydrogen chloride and of perchloric acid are measured by acid-based titration, the amount of sodium chloride and of calcium chloride by argentimetric titration, and the dichloropropanol content by vapor-phase chromatography. The water content is calculated by difference. The phase separating times and the compositions of the aqueous and organic phases are reported in Tables 1 to 4.

EXAMPLES 19 TO 22

In Accordance with the Invention

The procedure of the preceding examples was repeated using 2,3-dichloropropan-1-ol and aqueous solutions of perchloric acid and sodium chloride, the concentrations of which are given in Tables 5 and 6. The phase separating times and the compositions of the aqueous and organic phases are reported in Tables 5 and 6.

TABLE 1

| | Additive HCl (mol/l) | Aqueous phase | | | Organic phase | | | |
|---|---|---|---|---|---|---|---|---|
| Example | | 1,3-DCPol (% g/g) | Water (% g/g) | HCl (% g/g) | 1,3-DCPol (% g/g) | Water (% g/g) | HCl (% g/g) | Phase separating time |
| 1 | 0.0001 | 15.92 | 84.09 | | 86.50 | 13.50 | | less than a minute |
| 2 | 0.001 | 15.14 | 84.86 | | 86.30 | 13.70 | | less than a minute |
| 3 | 0.01 | 16.24 | 83.72 | 0.037 | 86.45 | 13.55 | 0.004 | less than a minute |
| 4 | 0.1 | 15.84 | 83.82 | 0.345 | 86.73 | 13.25 | 0.018 | less than a minute |
| 5 | 1 | 15.93 | 80.82 | 3.252 | 87.98 | 11.85 | 0.167 | less than a minute |

1,3-DCPol = 1,3-dichloropropan-2-ol

TABLE 2

| | Additive HClO4 (mol/kg) | Aqueous phase | | | Organic phase | | | |
|---|---|---|---|---|---|---|---|---|
| Example | | 1,3-DCPol (% g/g) | Water (% g/g) | HClO4 (% g/g) | 1,3-DCPol (% g/g) | Water (% g/g) | HClO4 (% g/g) | Phase separating time |
| 6 | 0.001 | 15.29 | 84.71 | | 86.30 | 13.70 | | Organic phase clouds, separation approximately 3 h |
| 7 | 0.01 | 15.23 | 84.66 | 0.115 | 86.50 | 13.50 | | Organic phase clouds, separation approximately 3 h |
| 8 | 0.1 | 15.26 | 83.76 | 0.980 | 86.25 | 13.65 | 0.099 | less than a minute |
| 9 | 1 | 21.24 | 70.67 | 8.087 | 81.75 | 16.50 | 1.755 | less than a minute |
| 10 | 2 | 38.19 | 50.98 | 10.829 | 69.20 | 25.26 | 5.536 | less than a minute |

1,3-DCPol = 1,3-dichloropropan-2-ol

TABLE 3

| | Additive NaCl (mol/kg) | Aqueous phase | | | Organic phase | | | |
|---|---|---|---|---|---|---|---|---|
| Example | | 1,3-DCPol (% g/g) | Water (% g/g) | NaCl (% g/g) | 1,3-DCPol (% g/g) | Water (% g/g) | NaCl (% g/g) | Phase separating time |
| 11 | 0.0001 | 14.80 | 85.20 | | 86.70 | 13.30 | | Aqueous phase clouds, separation more than 6 h |
| 12 | 0.001 | 14.34 | 85.66 | | 86.80 | 13.20 | | Aqueous phase clouds, separation more than 6 h |
| 13 | 0.1 | 14.63 | 84.69 | 0.677 | 87.15 | 12.85 | | less than a minute |
| 14 | 1 | 10.03 | 84.18 | 5.792 | 89.21 | 10.70 | 0.086 | less than a minute |
| 15 | 2 | 6.64 | 81.16 | 12.205 | 90.94 | 8.95 | 0.105 | less than a minute |
| 16 | 3 | 2.28 | 72.98 | 24.734 | 90.21 | 9.64 | 0.148 | less than a minute |

1,3-DCPol = 1,3-dichloropropan-2-ol

TABLE 4

| Example | Additive CaCl2 (mol/kg) | Aqueous phase | | | Organic phase | | | Phase separating time |
|---|---|---|---|---|---|---|---|---|
| | | 1,3-DCPol (% g/g) | Water (% g/g) | CaCl2 (% g/g) | 1,3-DCPol (% g/g) | Water (% g/g) | CaCl2 (% g/g) | |
| 17 | 0.9 | 8.20 | 82.170 | 9.63 | 90.22 | 9.75 | 0.027 | less than a minute |
| 18 | 2.7 | 2.02 | 68.360 | 29.61 | 95.96 | 4.00 | 0.043 | less than a minute |

1,3-DCPol = 1,3-dichloropropan-2-ol

TABLE 5

| Example | Additive HClO4 (mol/kg) | Aqueous phase | | | Organic phase | | | Phase separating time |
|---|---|---|---|---|---|---|---|---|
| | | 2,3-DCPol (% g/g) | Water (% g/g) | HClO4 (% g/g) | 2,3-DCPol (% g/g) | Water (% g/g) | HClO4 (% g/g) | |
| 19 | 1 | 13.65 | 78.09 | 8.26 | 85.21 | 13.40 | 1.39 | Organic phase clouds, separation approximately 1 h |
| 20 | 2 | 21.37 | 64.88 | 13.75 | 75.61 | 19.60 | 4.79 | Organic phase clouds, separation approximately 1 h |

2,3-DCPol = 2,3-dichloropropan-1-ol

TABLE 6

| Example | Additive NaCl (mol/kg) | Aqueous phase | | | Organic phase | | | Phase separating time |
|---|---|---|---|---|---|---|---|---|
| | | 2,3-DCPol (% g/g) | Water (% g/g) | NaCl (% g/g) | 2,3-DCPol (% g/g) | Water (% g/g) | NaCl (% g/g) | |
| 21 | 1 | 8.26 | 85.76 | 5.98 | 90.59 | 9.35 | 0.055 | less than a minute |
| 22 | 2 | 5.91 | 83.03 | 11.06 | 91.72 | 8.20 | 0.076 | less than a minute |

2,3-DCPol = 2,3-dichloropropan-1-ol

The invention claimed is:

1. A process for preparing dichloropropanol, comprising:
(a) reacting glycerol, an ester of glycerol or a mixture thereof with a chlorinating agent in the presence of an organic acid so as to give a mixture comprising dichloropropanol, at least one dichloropropanol ester, and water;
(b) subjecting at least a fraction of the mixture obtained in (a) to a distillation and/or stripping treatment so as to give a part concentrated with water, with dichloropropanol and with at least one dichloropropanol ester; and
(c) subjecting at least a fraction of the part obtained in (b) to a separating operation in the presence of at least one additive so as to give a portion concentrated with dichloropropanol and at least one dichloropropanol ester and comprising less than 40% by weight of water,
wherein the additive present in (c) comprises an inorganic acid, an inorganic salt or a mixture of the two and wherein said separating operation is a decantation having a decantation time of less than or equal to 120 minutes.

2. The process according to claim 1, wherein the portion concentrated with dichloropropanol and at least one dichloropropanol ester in (c) comprises less than 15% by weight of water.

3. The process according to claim 1, wherein the decantation is performed under the action of gravity.

4. The process according to claim 1, wherein the additive present in (c) is an inorganic acid selected from the group consisting of hydrogen halides, sulphuric, sulphurous, sulphydric, nitric, nitrous, phosphoric, phosphorous, perchloric, chloric, chlorous, hypochlorous, carbonic and boric acid and mixtures thereof.

5. The process according to claim 4, wherein the inorganic acid is hydrogen chloride and the amount of inorganic acid in the concentrated part obtained in (b) is greater than or equal to 0.01 g/kg and less than or equal to 170 g/kg.

6. The process according to claim 1, wherein the additive comprises an inorganic salt selected from the group consisting of metal halides, sulphates, hydrogen sulphates, sulphites, hydrogen sulphites, sulphides, hydrogen sulphides, nitrates, nitrites, phosphates, hydrogen phosphates, phosphites, hydrogen phosphites, perchlorates, chlorates, hypochlorites, carbonates, hydrogen carbonates, percarbonates, borates and perborates and mixtures thereof.

7. The process according to claim 6, wherein the inorganic salt is sodium chloride and the amount of salt in the concentrated part obtained in (b) is greater than or equal to 0.4 g/kg and less than or equal to 280 g/kg.

8. The process according to claim 1, wherein the decantation is carried out at a temperature greater than or equal to 10° C. and less than or equal to 100° C.

9. The process according to claim 1, wherein the amount of water in the concentrated portion obtained in (c) is less than or equal to 5% by weight.

10. The process according to claim 1, wherein the glycerol, the ester of glycerol or the mixture thereof is obtained starting from renewable raw materials.

11. The process according to claim 1, wherein the chlorinating agent comprises hydrogen chloride.

12. The process according to claim 11, wherein the hydrogen chloride is a combination of gaseous hydrogen chloride and an aqueous solution of hydrogen chloride, or an aqueous solution of hydrogen chloride.

13. The process according to claim 1, wherein the additive is present in the mixture obtained in step (a).

14. The process according to claim 1, further comprising preparation of epichlorohydrin by dehydrochlorination of the dichloropropanol.

15. The process according to claim 14, further comprising the preparation of an epoxy resin from the epichlorohydrin.

16. The process according to claim 1, wherein the decantation operation is carried out at a temperature greater than or equal to 4° C. and less than or equal to 100° C.

17. The process according to claim 1, wherein the decantation operation is carried out at a temperature greater than or equal to 10° C. and less than or equal to 70° C.

18. The process according to claim 1, wherein the decantation is carried out for a time less than or equal to 90 min.

19. The process according to claim 1, wherein the decantation is carried out for a time less than or equal to 60 min.

20. The process according to claim 1, wherein the amount of acid in the fraction of the concentrated part separated off in (b) and subjected to the decantation operation is greater than or equal to 0.01 g/kg and less than or equal to 110 g/kg.

21. The process according to claim 1, wherein the amount of acid in the fraction of the concentrated part separated off in (b) and subjected to the decantation operation is greater than or equal to 3 g/kg and less than or equal to 80 g/kg.

22. The process according to claim 1, wherein the amount of acid in the fraction of the concentrated part separated off in (b) and subjected to the decantation operation is greater than or equal to 25 g/kg and less than or equal to 65 g/kg.

* * * * *

UNITED STATES PATENT AND TRADEMARK OFFICE
CERTIFICATE OF CORRECTION

PATENT NO. : 7,557,253 B2
APPLICATION NO. : 11/915056
DATED : July 7, 2009
INVENTOR(S) : Patrick Gilbeau

Page 1 of 1

It is certified that error appears in the above-identified patent and that said Letters Patent is hereby corrected as shown below:

Column 6, line 52, "decantaion" should read "decantation".

Signed and Sealed this

Eighth Day of December, 2009

David J. Kappos
*Director of the United States Patent and Trademark Office*